US011285264B2

United States Patent
Holmqvist

(10) Patent No.: US 11,285,264 B2
(45) Date of Patent: Mar. 29, 2022

(54) MIX AND TRIGGERING ASSEMBLY FOR A MEDICAMENT DELIVERY DEVICE

(71) Applicant: SHL MEDICAL AG, Zug (CH)

(72) Inventor: Anders Holmqvist, Värmdö (SE)

(73) Assignee: SHL MEDICAL AG, Zug (CH)

( * ) Notice: Subject to any disclaimer, the term of this patent is extended or adjusted under 35 U.S.C. 154(b) by 386 days.

(21) Appl. No.: 16/683,758

(22) Filed: Nov. 14, 2019

(65) Prior Publication Data
US 2020/0155761 A1 May 21, 2020

(30) Foreign Application Priority Data
Nov. 20, 2018 (EP) ........................................ 8207318

(51) Int. Cl.
*A61M 5/19* (2006.01)
*A61J 1/20* (2006.01)
(Continued)

(52) U.S. Cl.
CPC .............. *A61M 5/19* (2013.01); *A61J 1/1406* (2013.01); *A61J 1/2013* (2015.05); *A61J 1/2093* (2013.01);
(Continued)

(58) Field of Classification Search
CPC .. A61M 5/20; A61M 5/2033; A61M 5/31525; A61M 5/31528; A61M 5/31548;
(Continued)

(56) References Cited

U.S. PATENT DOCUMENTS

2002/0183690 A1\* 12/2002 Arnisolle ............ A61M 5/2066
604/83
2013/0218074 A1 8/2013 Holmqvist et al.
(Continued)

*Primary Examiner* — Bhisma Mehta
*Assistant Examiner* — Hong-Van N Trinh
(74) *Attorney, Agent, or Firm* — McDonnell Boehnen Hulbert & Berghoff LLP

(57) ABSTRACT

A mix and triggering assembly for a medicament delivery device, comprising: a housing structure having a proximal end and a distal end, a delivery member cover, a rotator sleeve, and a triggering member configured to be rotatably locked with the rotator sleeve and the delivery member cover, the triggering member being configured to move axially relative to the rotator sleeve, wherein the delivery member cover, the rotator sleeve and the triggering member are configured to be received by the housing structure, the delivery member cover being configured to extend from the proximal end of the housing structure, wherein the delivery member cover, the rotator sleeve and the triggering member are rotatably arranged relative to the housing structure, wherein the housing structure has a thread structure and the rotator sleeve and the triggering member are configured to be in a threaded connection with the thread structure in a ready to mix position of the triggering member, preventing irrotational axial movement of the triggering member relative to the housing structure towards the distal end of the housing structure, wherein rotation of the delivery member cover relative to the housing structure causes the rotator sleeve and the triggering member to be screwed from the ready to mix position towards the distal end of the housing structure until the triggering member reaches a dose setting position, in which the triggering member is configured to be released from engagement with the thread structure, enabling irrotational axial movement of the triggering member further towards the distal end of the housing structure.

20 Claims, 12 Drawing Sheets

(51) Int. Cl.
*A61J 1/14* (2006.01)
*A61M 5/20* (2006.01)
*A61M 5/315* (2006.01)

(52) U.S. Cl.
CPC ...... *A61M 5/2033* (2013.01); *A61M 5/31528* (2013.01); *A61M 5/31551* (2013.01); *A61M 2005/2073* (2013.01)

(58) Field of Classification Search
CPC ............ A61M 5/3155; A61M 5/31551; A61M 2005/2073; A61M 2005/208; A61M 2005/206; A61M 5/24; A61M 2005/2013; A61M 5/326; A61M 2005/2492; A61M 5/3158; A61M 5/3159–5/31595; A61M 5/2066; A61M 5/2448; A61M 2005/2451; A61M 5/284; A61M 5/31596; A61M 5/3294; A61M 5/19; A61J 1/1406; A61J 1/2013; A61J 1/2093
See application file for complete search history.

(56) References Cited

U.S. PATENT DOCUMENTS

2014/0323963 A1 10/2014 West
2017/0189619 A1 7/2017 Constantineau et al.

\* cited by examiner

MIX AND TRIGGERING ASSEMBLY FOR A MEDICAMENT DELIVERY DEVICE

CROSS REFERENCE TO RELATED APPLICATIONS

The present application claims priority to European Patent Application No. 18207318.9 filed Nov. 20, 2018, which is herewith incorporated by reference into the present application.

TECHNICAL FIELD

The present disclosure generally relates to medicament deliver devices, in particular to medicament delivery devices with medicament mixing capability.

BACKGROUND

Medicament delivery devices may have a medicament container which for hygienic reasons is sealed prior to use when it is pierced by a double-edged needle.

An example of a medicament delivery device of this type is disclosed in WO2013/048310. The device has an initial locked state in which a cap is arranged at the proximal end of the device. An intermediate priming state is obtained by removing the cap.

Medicament delivery devices such as injectors may be used for administering medicaments with a relatively short shelf life. Nevertheless, medicament delivery devices containing such medicaments may sometimes have to be stored for a period of time that is longer than the shelf life of the medicament. In order to be able to fulfil such requirements, the medicament may be provided in e.g. freeze-dried form which has longer shelf life than the medicament in liquid form in an isolated chamber inside the medicament container of the medicament delivery device. The medicament container then typically also comprises another chamber containing a liquid such as water separated from the chamber containing the freeze-dried medicament. These types of medicament delivery devices may be designed to enable a user to mix the freeze-dried medicament and the liquid prior to medicament administration to obtain a liquid medicament.

The device disclosed in WO2013/048310 is not designed for mixing purposes.

U.S. Pat. No. 4,983,164 discloses an automatic two-chamber injector for mixing and injecting a medical solution. The injector comprises a barrel having a first end with a receiving portion for an injection needle, the portion being sealed prior to use, and a second end with a displaceable plunger. The barrel comprises two chambers separated by a migration-proof membrane. The membrane is adapted to rupture when the plunger is displaced towards the first end of the barrel.

WO2016/190980 discloses a removable cap for use with an auto-injector device. Removal of the cap triggers an actuating assembly that can cause an automatic mixing of medicament components in an auto-injector device and/or place the auto-injector in a state to be used.

SUMMARY

A general object of the present disclosure is to provide mix and triggering assembly for a medicament delivery device which solves or at least mitigates problems of the prior art.

There is hence according to a first aspect of the present disclosure provided a mix and triggering assembly for a medicament delivery device, comprising: a housing structure having a proximal end and a distal end, a delivery member cover, a rotator sleeve, and a triggering member configured to be rotatably locked with the rotator sleeve and the delivery member cover, the triggering member being configured to move axially relative to the rotator sleeve, wherein the delivery member cover, the rotator sleeve and the triggering member are configured to be received by the housing structure, the delivery member cover being configured to extend from the proximal end of the housing structure, wherein the delivery member cover, the rotator sleeve and the triggering member are rotatably arranged relative to the housing structure, wherein the housing structure has a thread structure and the rotator sleeve and the triggering member are configured to be in a threaded connection with the thread structure in a ready to mix position of the triggering member, preventing irrotational axial movement of the triggering member relative to the housing structure towards the distal end of the housing structure, wherein rotation of the delivery member cover relative to the housing structure causes the rotator sleeve and the triggering member to be screwed from the ready to mix position towards the distal end of the housing structure until the triggering member reaches a dose setting position, in which the triggering member is configured to be released from engagement with the thread structure, enabling irrotational axial movement of the triggering member further towards the distal end of the housing structure.

Linear irrotational actuation of the delivery member cover before mixing may thereby be prevented. Accidental exposure of a delivery member, such as a needle, may thereby be prevented before mixing. Additionally, accidental triggering of a mixing procedure may also be prevented, since rotation of the delivery member cover to screw the rotator sleeve and the triggering member towards the distal end of the housing structure requires more effort than irrotational linear movement.

The mix and triggering assembly may comprise a medicament container holder configured to be axially and rotationally locked relative to the rotator sleeve. Movement of the rotator sleeve towards the distal end of the housing structure hence causes the medicament container holder to follow the motion of the rotator sleeve.

The mix and triggering assembly may comprise a plunger rod having a proximal end portion configured to extend into the medicament container holder, and in particular into a medicament container. The medicament container holder may be connected to a double-edged needle having a distally pointing needle portion, a proximal chamber containing a freeze-dried medicament, wherein the distally pointing needle portion extends into the proximal chamber, a distal chamber containing liquid, a plunger separating the proximal chamber and the distal chamber, and at least one bypass channel arranged proximally from the plunger. The plunger rod may be configured to be axially fixed relative to the housing structure when the rotator sleeve and the triggering member are screwed from the ready to mix position to the dose setting position. The medicament container holder will hence receive a greater portion of the proximal end portion of the plunger rod during this motion, increasing the pressure in the distal chamber. This causes the plunger to move towards the proximal end of the housing structure, until it reaches the at least one bypass channel, which enables liquid to flow in the proximal direction past the plunger. The freeze-dried medicament and the liquid is thereby mixed when the rotator sleeve and the triggering member are screwed from the ready to mix position to the dose setting position.

According to one embodiment the delivery member cover is axially locked relative to the triggering member, wherein the thread structure has an engagement member configured to snap-fit with a triggering member thread structure of the triggering member to prevent irrotational axial movement of the triggering member from the ready to mix position to the dose setting position. Since the triggering member is axially locked relative to the delivery member cover it can be ensured that the delivery member cover cannot be accidentally irrotationally moved in the axial direction further into the housing before mixing. It may thereby be ensured that a delivery member covered by the delivery member cover will not be exposed in at this stage.

According to one embodiment the triggering member is configured to be biased towards the proximal end of the housing structure, and wherein in an initial default position the delivery member cover is configured to be axially locked relative to the housing structure in a partly received position in the housing structure, wherein the triggering member is configured to move axially towards the proximal end of the housing structure when the delivery member cover is released from the initial default position to set the triggering member from the initial default position to the ready to mix position, in which the delivery member cover extends proximally further from the housing structure relative to the partly received position. Hence, it may be ensured that the delivery member cover will return to the ready to mix position, in which it covers a delivery member. The delivery member cover may for example be axially locked relative to the housing structure due to a front cap being mounted to a delivery member assembly, causing the biased delivery member cover to be received further into the housing. When the front cap is removed from a delivery member, the delivery member cover is hence able to return to its most proximal position relative to the housing structure.

According to one embodiment the engagement member is configured to allow irrotational axial movement of the triggering member from the initial default position towards the proximal end of the housing structure to move to the ready to mix position. Since the triggering member is rotationally locked relative to the rotator sleeve, but configured to move axially relative to the rotator sleeve, the triggering member and hence the delivery member cover are able to move relative to the housing structure. The delivery member cover will hence be able to obtain a position in which it covers a delivery member prior to mixing.

According to one embodiment the rotator sleeve has a blocking structure configured to engage with a thread segment of the thread structure of the housing structure when the triggering member is in the dose setting position to prevent rotation of the rotator sleeve back towards the proximal end of the housing structure. The mixing process in the medicament container may hence be better controlled.

According to one embodiment the thread structure includes a plurality of disjoint thread segments in the circumferential direction, wherein the blocking structure is configured to bear against a radial edge of a thread segment to prevent rotation of the rotator sleeve back towards the proximal end of the housing structure.

According to one embodiment the triggering member has two legs and the rotator sleeve has chamfered faces, wherein the legs are configured to extend along a respective chamfered face towards the proximal end of the housing structure. This design enables relative axial movement between the triggering member and the rotator sleeve but prevents relative rotation between these two components.

According to one embodiment the triggering member has axially extending barriers configured to delimit circumferential movement of the engagement member when the triggering member is in the dose setting position, thereby preventing further rotation of the triggering member towards the distal end of the housing structure. The axial position of the triggering member, as determined by rotation of the triggering member relative to the housing structure, may thereby be controlled. Since the rotating motion and the resulting axial movement of the triggering member is involved in the mixing procedure, an end position of the components involved in the mixing procedure may thereby be set.

According to one embodiment the axially extending barriers pairwise form part of a proximal end portion of a respective leg of the triggering member.

According to one embodiment each leg has a planar portion arranged between the pairs of barriers to enable linear movement of the engagement member between the pairs of barriers of a leg. The triggering member may thereby be able to move further towards the distal end of the housing structure and move relative to the rotator sleeve, in order to initiate medicament delivery.

One embodiment comprises a clutch member and a dose knob configured to be rotationally locked with the clutch member, wherein the rotator sleeve is configured to push the clutch member towards the distal end of the housing structure when the triggering member is moved towards the dose setting position, causing the clutch member to move distally inside the housing structure from a first position in which it is rotationally locked with the housing structure to a second position in which it is able to rotate relative to the housing structure, enabling rotation of the dose knob relative to the housing structure. A dose may thereby be set by means of the dose knob when the clutch member is in the second position. The dose knob may for example be configured to set a single dose, or one of several doses. The dose knob may thus according to one example be a variable dose knob.

According to one embodiment the clutch member has a triggering member blocking structure configured to block the triggering member from movement from the dose setting position towards the distal end of the housing structure when the clutch member is in the first position.

According to one embodiment the dose knob is configured to rotate the clutch member such that the triggering member blocking structure is rotated and releases the triggering member, enabling the triggering member to move towards the distal end of the housing structure. The triggering member may be configured to initiate medicament administration by irrotational axial movement from the dose setting position towards the distal end of the housing structure. The triggering member blocking structure may hence prevent initiation of medicament administration until the dose knob is rotated to set the dose.

One embodiment comprises a rotator and a plunger rod, wherein the triggering member is configured to cause rotation of the rotator when the delivery member cover moves the triggering member from the dose setting position towards the distal end of the housing structure, releasing the plunger rod.

There is according to a second aspect of the present disclosure provided a medicament delivery device comprising a mix and triggering assembly according to the first aspect.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc.", unless explicitly stated otherwise.

BRIEF DESCRIPTION OF THE FIGURES

The specific embodiments of the inventive concept will now be described, by way of example, with reference to the accompanying drawings, in which.

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

In the present disclosure, when the term "distal direction" is used, this refers to the direction pointing away from the dose delivery site during use of the medicament delivery device. When the term "distal part/end" is used, this refers to the part/end of the delivery device, or the parts/ends of the members thereof, which under use of the medicament delivery device is/are located furthest away from the dose delivery site. Correspondingly, when the term "proximal direction" is used, this refers to the direction pointing towards the dose delivery site during use of the medicament delivery device. When the term "proximal part/end" is used, this refers to the part/end of the delivery device, or the parts/ends of the members thereof, which under use of the medicament delivery device is/are located closest to the dose delivery site. Further, the terms "longitudinal", "longitudinally", "axially" and "axial" refer to a direction extending from the proximal end to the distal end and along the device or components thereof, typically in the direction of the longest extension of the device and/or component.

Similarly, the terms "transverse", "transversal" and "transversally" refer to a direction generally perpendicular to the longitudinal direction.

Figure 1:
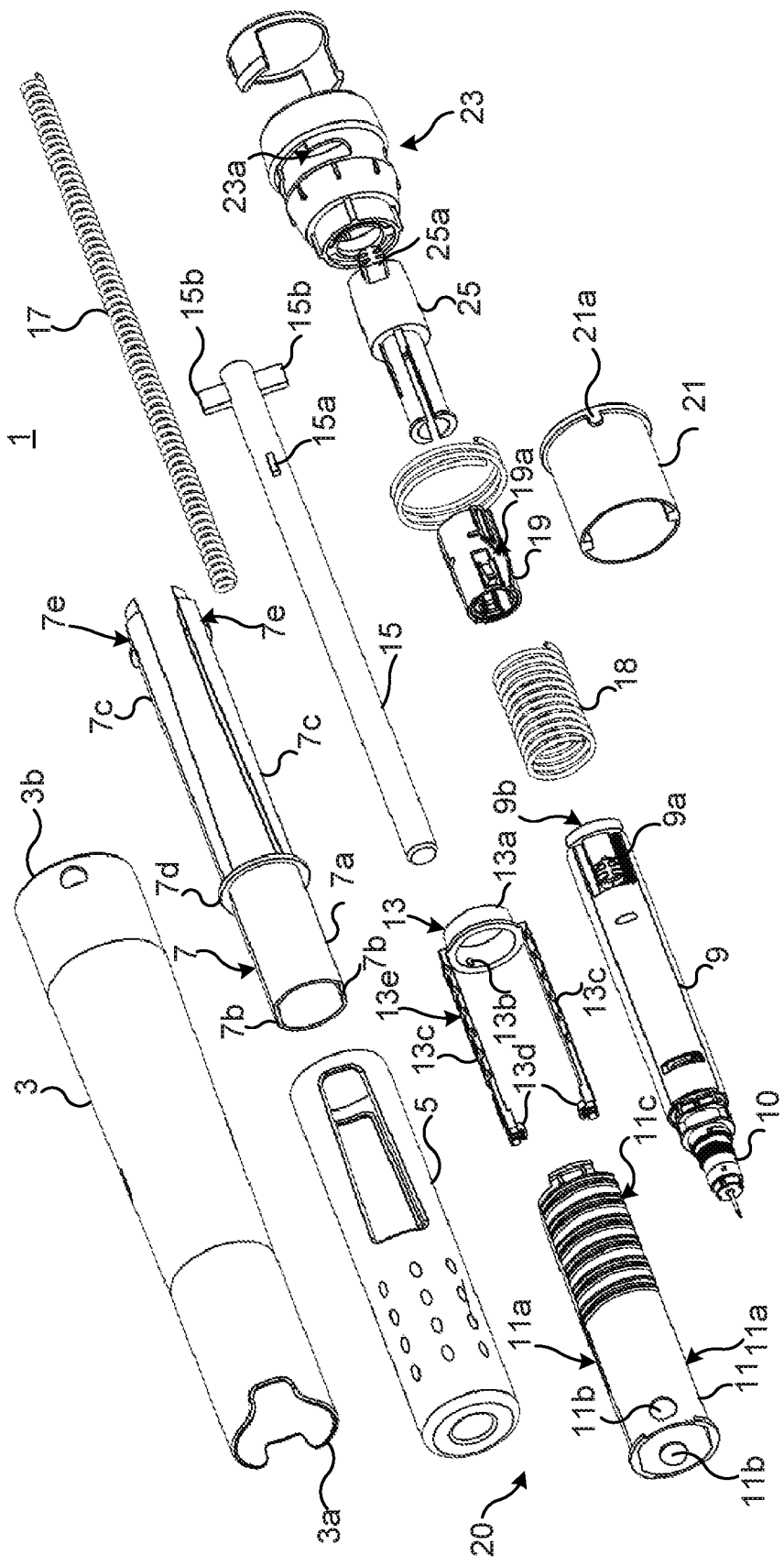
FIG. 1 is an exploded view of an example of a medicament delivery device.

FIG. 1 is an exploded view of an example of a medicament delivery device 1. The exemplified medicament delivery device is an injector, in particular an auto-injector or a semi-automatic injector.

The medicament delivery device 1 comprises an elongated housing structure 3 having a proximal end 3a and a distal end 3b, a delivery member cover 5, a coupling sleeve 7, a medicament container holder 9 configured to hold a medicament container, a delivery member assembly 10 configured to be connected to the medicament container holder 9, a rotator sleeve 11, a triggering member 13, a plunger rod 15, a first resilient member 17, such as a spring, configured to be received by the plunger rod 15, a second resilient member 18, such as a spring, a rotator 19, a clutch member 21, and a dose knob 23.

The housing structure 3, the delivery member cover 5, the rotator sleeve 11 and the triggering member 13 form or form part of a mix and triggering assembly 20.

The proximal end 3a of the housing structure 3 has a proximal opening. The housing structure 3 is configured to receive a portion of the delivery member cover 5 through the proximal opening. In a mounted state, a portion of the delivery member cover 5 extends from the proximal opening. The delivery member cover 5 is configured to be movable axially inside the housing structure 3.

The housing structure 3 is configured to receive the coupling sleeve 7. The coupling sleeve 7 is configured to be arranged coaxially with the delivery member cover 5 inside the delivery member cover 5. The coupling sleeve 7 is configured to be rotationally and axially locked relative to the delivery member cover 5.

The exemplified coupling sleeve 7 has a proximal closed portion 7a which is closed in the circumferential direction. The closed portion 7a may have a generally cylindrical shape with opposing chamfered faces 7b. The coupling sleeve 7 has two coupling sleeve legs 7c extending in the distal direction from the closed portion 7a. The two coupling sleeve legs 7c are configured to extend towards the distal end 3a of the housing structure 3. The coupling sleeve 7 has a radial flange 7d separating the closed portion 7a and the coupling sleeve legs 7c. The flange 7d is configured to engage with an inner surface structure of the delivery member cover 5 to prevent axial displacement in the distal direction of the coupling sleeve 7 relative to the delivery member cover 5.

The coupling sleeve 7 is configured to receive the medicament container holder 9.

The triggering member 13 has an annular distal end portion 13a. The annular distal end portion 13a has an inner surface provided with radially inwards extending rotator engagement structures 13b, of which one is visible in FIG. 1. The rotator 19 has guide tracks or cam surfaces 19a and the rotator engagement structures 13b are configured to cooperate with the guide tracks 19a to translate axial irrotational movement of the triggering member 13 to a rotation of the rotator 19.

The triggering member 13 has two legs 13c extending in the proximal direction from the annular distal end portion 13a. Each leg 13c is provided with a respective radial protrusion 13d extending radially inwards.

The triggering member 13 is configured to engage with the coupling sleeve 7. The coupling sleeve 7 and the triggering member 13 are configured to be axially and rotationally locked relative to each other. The exemplified coupling sleeve 7 has radial openings 7e configured to engage with a respective one of the radial protrusions 13d. The coupling sleeve 7 and the triggering member 13 thereby become rotationally and axially locked to each other.

The rotator sleeve 11 has opposing chamfered faces 11a. The legs 13c of the triggering member 13 are configured to run along a respective chamfered face. The rotator sleeve 11 also has two axial slits 11d, each slit 11d extending along a respective chamfered face 11a. Each slit 11d is configured to receive a respective radial protrusion 13d, which also engage with the coupling sleeve 7. The axial length of the slits 11d delimits the axial movement of the triggering member 13 relative to the rotator sleeve 11. The arrangement of the radial protrusions 13d in the slits 11d prevents rotation of the triggering member 13 relative to the rotator sleeve 11. The annular distal end portion 13a is configured to be arranged distally from the rotator sleeve 11, with the legs 13c extending in the proximal direction.

The rotator sleeve 11 has radial openings 11b and the medicament container holder 9 has radially outwards extending protrusions 9a configured to engage with a respective one of the radial openings 11b. The rotator sleeve 11 and the medicament container holder 9 are hence configured to be axially and rotationally locked relative to each other.

Since the rotator sleeve 11 is rotationally locked with the medicament container holder 9, the triggering member 13 is rotationally locked with the rotator sleeve 11, and the triggering member 13 is rotationally locked with the coupling sleeve 7 which is rotationally locked with the delivery member cover 5, all of these components are rotationally locked relative to the delivery member cover 5. Additionally, the delivery member cover 5, the coupling sleeve 7 and the rotator sleeve 11 are axially locked relative to each other. The triggering member 13 and the medicament container holder 9 are however under certain conditions able to move axially relative to the mentioned components, as will be made clear herein.

The housing structure 3 has an inner surface provided with a thread structure (not shown in FIG. 1). The rotator sleeve 11 has external rotator sleeve threads 11c configured to cooperate with the thread structure of the housing structure 3. The triggering member 13 has external triggering member threads 13e configured to cooperate with the thread structure of the housing structure 3. In particular, when the triggering member 13 maximally receives the rotator sleeve 11 between its legs 13c, the rotator sleeve threads 11c and the triggering member threads 13e are aligned, forming a common threaded structure configured to cooperate with the thread structure of the housing structure 3. The legs 13c have a curved outer structure in the circumferential direction, essentially completing the circular shape of the rotator sleeve 11 and the triggering member 13 in an assembled state.

The medicament container holder 9 has an axial distal opening 9b. The plunger rod 15 is configured to be received by the medicament container holder 9. In particular, a proximal end portion of the plunger rod 15 is configured to extend into the medicament container holder 9 through the distal opening 9b. The plunger rod 9 is configured to be biased in the proximal direction by means of the first resilient member 17. The plunger rod 15 has radially protruding stop members 15a. The rotator 19 is configured to receive a portion of the plunger rod 9 which is provided with the stop members 15a. The rotator 19 has corresponding inner stop surfaces configured to bear against the stop members 15a to prevent the proximally biased plunger rod 15 from moving in the proximal direction further into the medicament container holder 9 and thus further into a medicament container held by the medicament container holder 9. When the triggering member 13 is moved in the distal direction, as will be explained in detail in the following, the rotator engagement structures 13b will be moved distally in the guide tracks 19a causing linear motion of the triggering member 13 to be translated to a rotation of the rotator 19. The stop surfaces will thereby be rotated relative to the stop members 15a and disengage from the stop members 15a, allowing the stop members 15a and thus the plunger rod 15 to move proximally through the rotator 19.

The plunger rod 15 has radially outwards extending dose setting protrusions 15b configured to cooperate with the dose knob 23. The size of the dose to be administered may thereby be set.

The exemplified clutch member 21 has an essentially cylindrical shape. The clutch member 21 is configured to engage with the housing structure 3. Hereto, the clutch member 21 has a housing structure engagement structure 21a, in this example a radially outwards extending protrusion, configured to engage with a corresponding structure of the inner surface of the housing structure 3 to prevent rotation of the clutch member 21 relative to the housing structure 3. The clutch member 21 is configured to be pushed in the distal direction by the rotator sleeve 11 when the rotator sleeve 11 is moved towards the distal end 3b of the housing structure 3 to thereby release the engagement of the housing structure engagement structure 21a with the housing structure 3. This enables rotation of the clutch member 21 relative to the housing structure 3.

The clutch member 21 is configured to be connected to the dose knob 23. The clutch member 21 and the dose knob 23 are configured to be rotationally locked relative to each other. Thus, as long as the clutch member 21 is rotationally locked with the housing structure 3, the dose knob 23 is also prevented from being rotated. Hence, no dose may be set in this state. When the clutch member 21 has been released from its engagement with the housing structure 3, the clutch member 21 and the dose knob 3 may be rotated.

The exemplified medicament delivery device 1 comprises a plunger rod guide member 25. The plunger rod guide member 25 is configured to cooperate with the plunger rod 15. The plunger rod guide member 25 has recesses (not shown) configured to engage with the dose setting protrusions 15b of the plunger rod 15. The plunger rod guide member 25 has guide structures 25a configured to be received by recesses 23a of the dose knob 23. When the dose knob 23 is rotated, the guide structures 25a follow the rotation of the recesses 23a, thereby rotating the plunger rod guide member 25 and hence the plunger rod 15. In this manner, the stroke length of the plunger rod 15 for medicament administration may be set, and hence the dose may be set.

Figure 2:
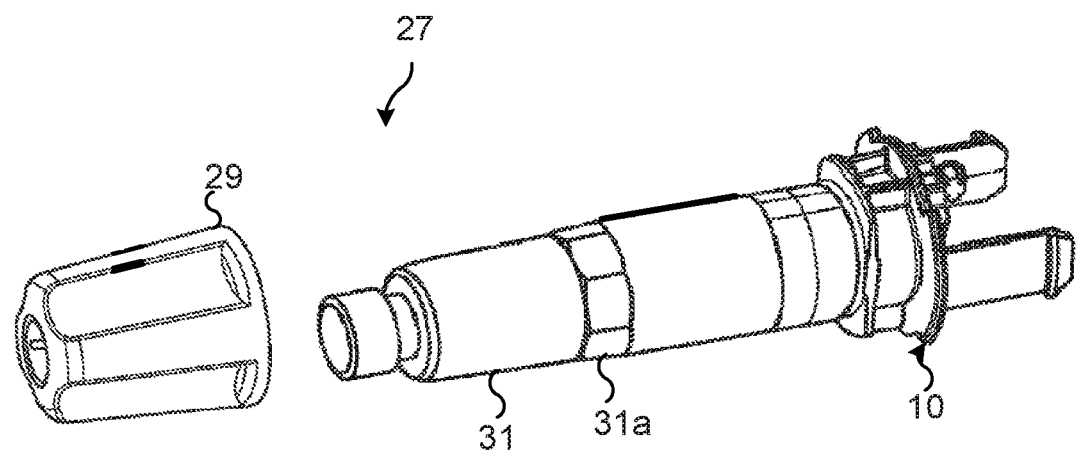
FIG. 2 shows a perspective view of an example of a front cap assembly.

With reference to FIG. 2, the exemplified medicament delivery device 1 comprises a front cap assembly 27 of the type disclosed in WO2013/048310. The front cap assembly 27 comprises a front cap 29 and an inner cap 31 configured to be threadedly engaged with the delivery member assembly 10, which also may be of the type disclosed in WO2013/048310. The front cap 29 has an inner polygonal surface portion configured to engage with a corresponding outer polygonal surface portion 31a of the inner cap 31. In the initial state or initial default position of the medicament delivery device 1, the inner cap 31 is mounted to the delivery member assembly 10 and the front cap 29 is mounted to the inner cap 31. Since the relatively large front cap 29 is assembled with the delivery member assembly 10 which normally is covered by the delivery member cover 5 which is biased in the proximal direction by the second resilient member 18, the delivery member cover 5 is pushed somewhat into the housing structure 3 by the front cap 29. The rotator sleeve 11, which is axially locked relative to the delivery member cover 5 has in this position its rotator sleeve threads 11c engaging with the thread structure of the housing structure 3. The delivery member cover 5 is hence axially locked relative to the housing structure 3 in the initial default position.

Figure 3:
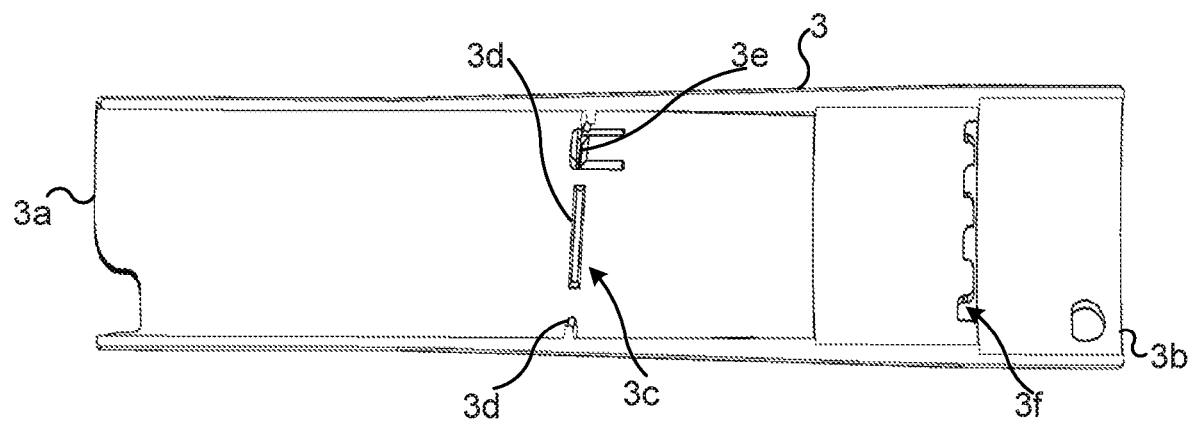
FIG. 3 is a sectional view of the housing structure of the medicament delivery device in FIG. 1.

FIG. 3 shows a longitudinal section of the housing structure 3. The housing structure 3 has an inner surface provided with the thread structure 3c. The thread structure 3c comprises a plurality of thread segments 3d. The thread segments 3d are disjoint in the circumferential direction.

The inner surface of the housing structure 3 is provided with an engagement member 3e. The engagement member 3e may be radially flexible. The engagement member 3e has an essentially radial surface in a direction from the proximal end 3a towards the distal end 3b, and a gradually increasing thickness in the direction from the distal end 3b towards the proximal end 3a. The engagement member 3e hence has a ramp shape in the direction from the distal end 3b towards the proximal end 3a. The housing structure 3 may be provided with for example two such engagement members 3e, for example spaced apart 180 degrees in the circumferential direction.

The inner surface of the housing structure 3 has one or more recesses 3f configured to receive the housing structure engagement structure 21a of the clutch member 21 to thereby rotationally lock the clutch member 21 with the housing structure 3.

Figure 4:
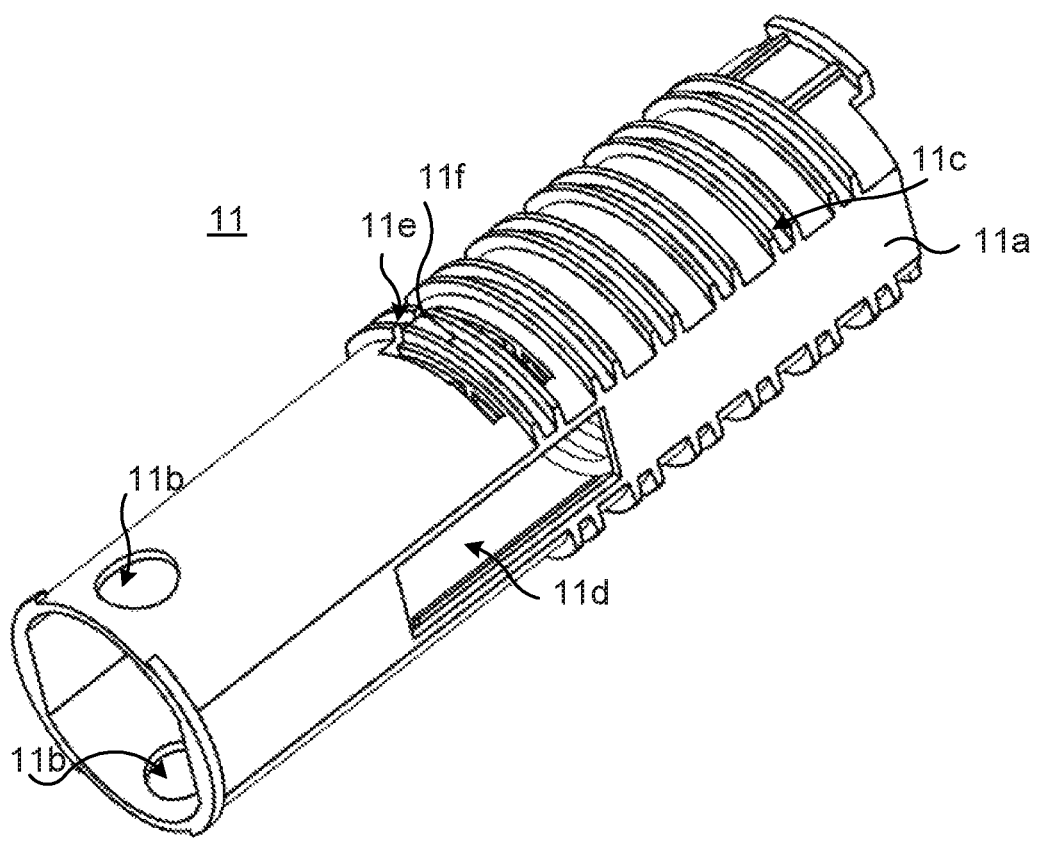
FIG. 4 shows a perspective view of a rotator sleeve of the medicament delivery device in FIG. 1.

FIG. 4 shows the rotator sleeve 11 in more detail. In particular, the slits 11d configured to receive a respective one of the radial protrusions 13d of the triggering member 13 are illustrated. The rotator sleeve 11 has a blocking structure 11e. The blocking structure 11e is provided in the most proximally located thread of the rotator sleeve threads 11c. In particular, the blocking structure 11e is formed by a discontinuity in the circumferential direction in the most proximal thread of the rotator sleeve threads 11c. The blocking structure 11e has a snap-fit functionality with the first thread segment 3d passing the blocking structure 11e when the rotator sleeve 11 is rotated relative to the housing structure 3.

The blocking portion 11 may have a ramp structure 11f with a radial or essentially radial surface that prevents a thread segment 3d of the housing structure 3 to move backwards once it has passed the blocking structure 11e during rotation. The blocking portion 11 hence prevents backwards rotation of the rotator sleeve 11 when a thread segment 3d has moved past the blocking structure 11e.

Figure 5:
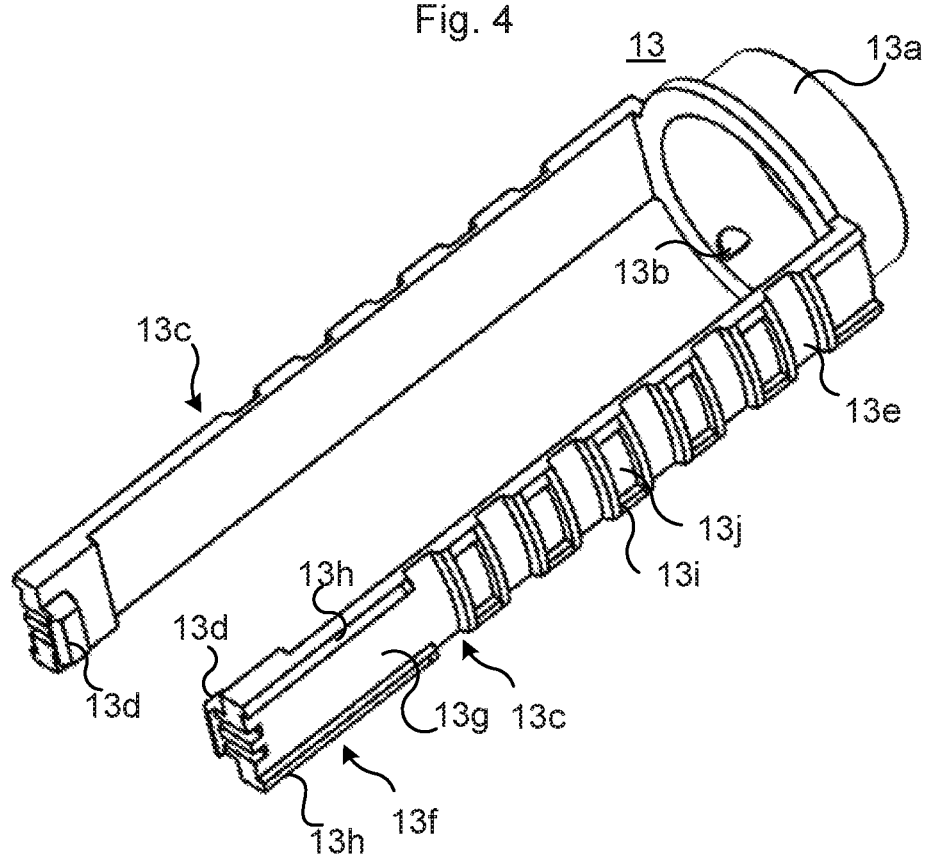
FIG. 5 shows a perspective view of a triggering member of the medicament delivery member in FIG. 1.

FIG. 5 depicts the triggering member 13 in more detail. The legs 13c have proximal end portions 13f which have axially extending planar portions 13g. The planar portions 13g are unthreaded. The legs 13c furthermore have axially extending barriers or ribs 13. For each leg 13c, the planar portion 13g extends between the corresponding two barriers 13h.

The triggering member 13 may comprise a plurality of elevated portions 13i each provided with a radial recess 13j. The elevated portions 13a and radial recesses 13j separates the triggering member threads 13e in the axial direction and hence form part of a triggering member thread structure of the triggering member 13. The recesses 13j are designed to receive an engagement member 3e, as shown in FIG. 5. Due to the specific ramp configuration of the engagement member 3e the triggering member 13 is prevented from irrotational axial movement in the distal direction as long as the engagement member 3e is arranged in a recess 13j. The design of the engagement members 3e however enables the triggering member 13 to be moved axially without rotation in the proximal direction.

Each engagement member 3e is configured run between two barriers 13h along a planar portion 13g. This situation occurs when the triggering member 13 and the rotator sleeve 11 have been rotated relative to the housing structure 3 such that the thread structure 3c of the housing structure 3 reaches the most proximal thread of the rotator sleeve 11 and a thread segment 3d has passed the blocking portion 11, as will be elaborated upon in the following.

Figure 6:
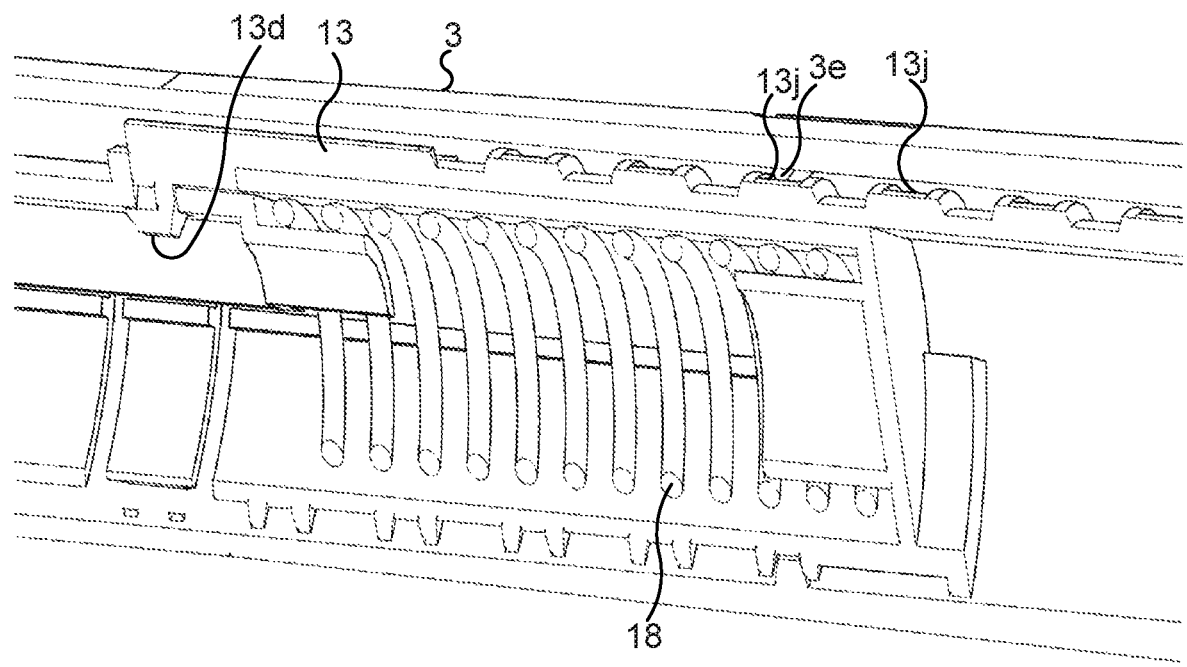
FIG. 6 shows a sectional view of the medicament delivery device in FIG. 1.
Figure 7:
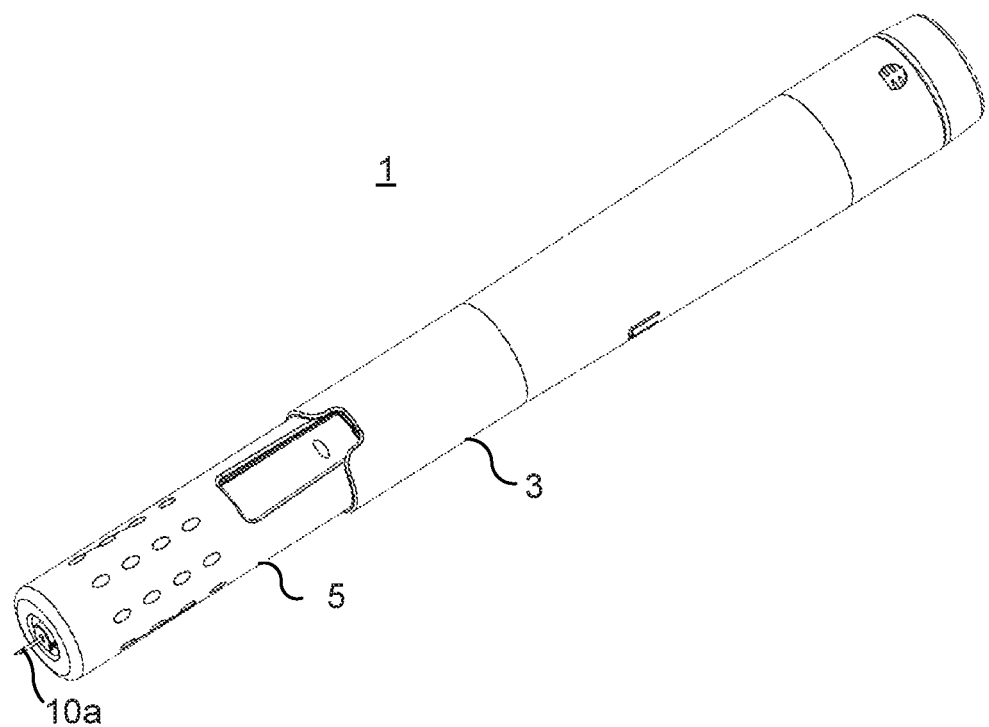
FIG. 7 is a perspective view of the medicament delivery device in FIG. 1 in an initial default state/position prior to mixing.
Figure 8:
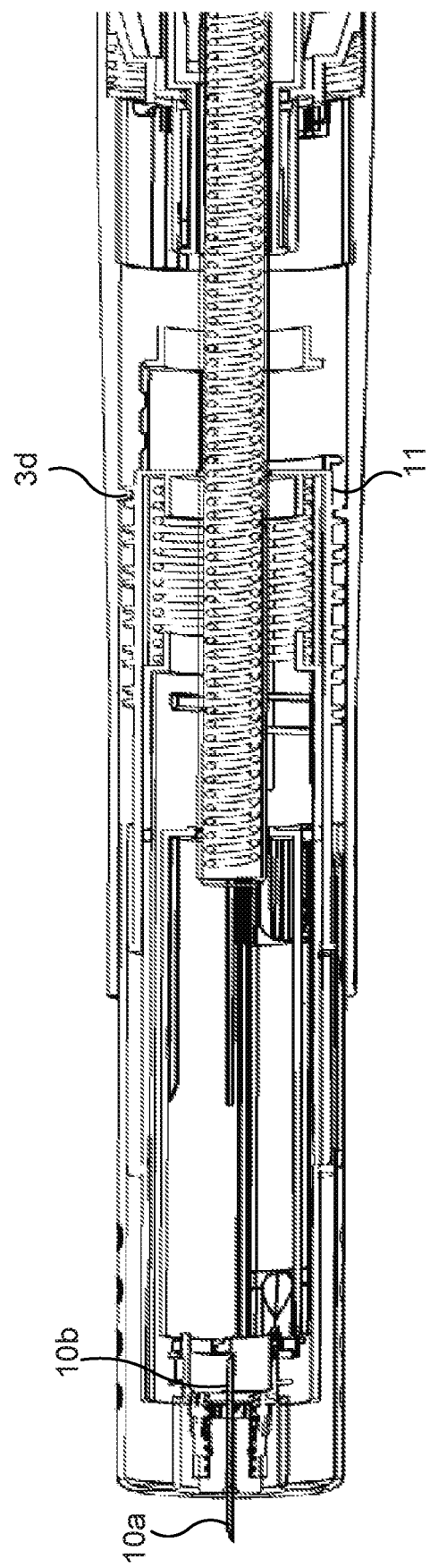
FIG. 8 is a longitudinal section of the medicament delivery device in FIG. 7.

FIG. 6 shows a perspective view of the medicament delivery device 1 in the initial default position. In this position, the front cap 29 and inner cap 31 are mounted to the to the delivery member assembly 10. The front cap 29 and the inner cap 31 are however not shown in FIG. 6. As shown in FIG. 7, the thread structure 3c, in particular a thread segment 3d is arranged in the most distally located thread of the rotator sleeve threads 11c in the initial default position. In the initial default position, the triggering member 13 is arranged in its most distal position relative to the rotator sleeve 11. The radial protrusions 13d of the legs 13c are hence arranged in their most distal position in the slits 11d, as shown in FIG. 8.

The delivery member assembly 10 comprises a double-edged needle including a proximally pointing needle portion 10a and a distally pointing needle portion 10b.

When the front cap 29 is unscrewed, the inner cap 31 is brought with it. Additionally, while the front cap 29 is being unscrewed, a delivery member unit, including the double-edged needle and a threaded needle housing holding the double-edged needle, of the delivery member assembly 10 is screwed in the distal direction to pierce a septum of the medicament container arranged in the medicament container holder 9.

Figure 9:
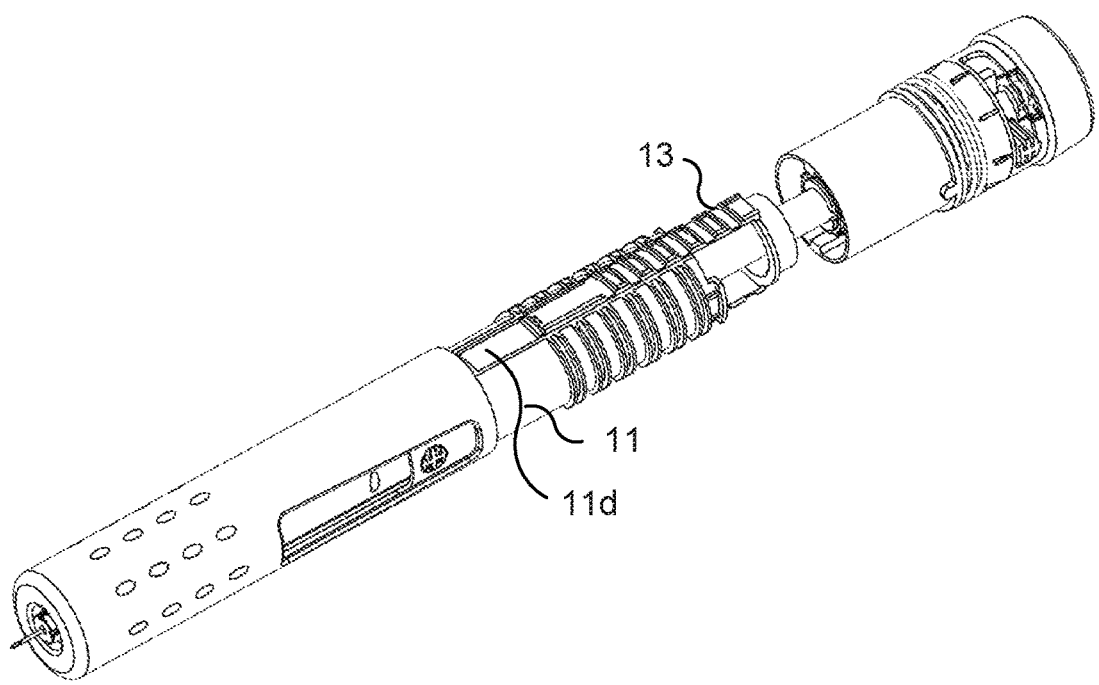
FIG. 9 is a perspective view of the medicament delivery device in FIG. 7 with the housing structure removed to expose the interior of the device.
Figure 10:
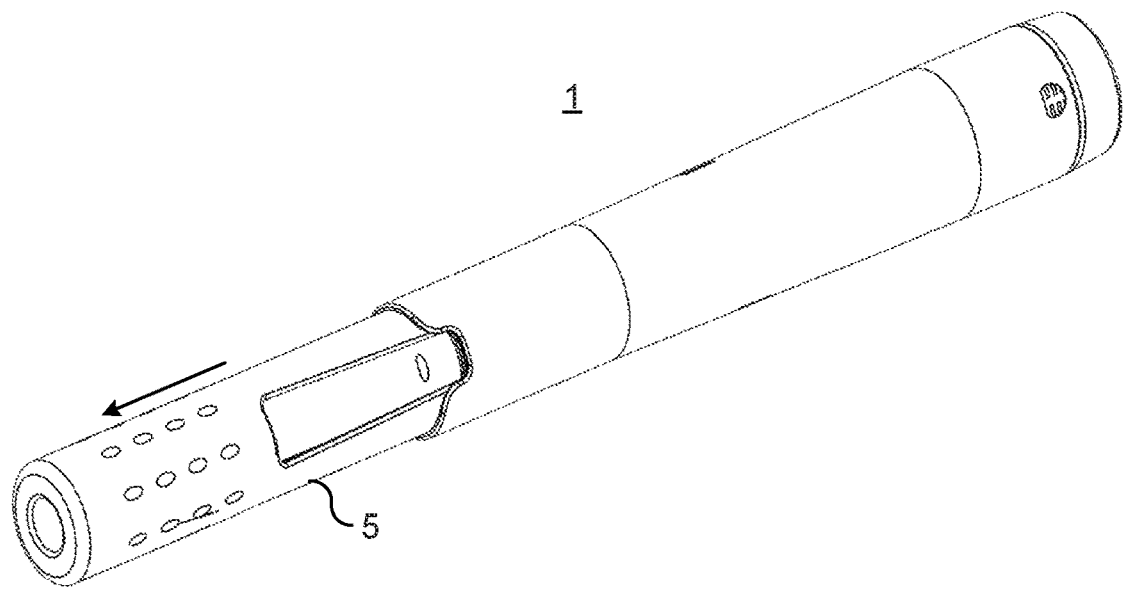
FIG. 10 is a perspective view of the medicament delivery device in FIG. 1 in a ready to mix state/position.

When using the medicament delivery device 1, the first operation carried out by a user is typically to remove the front cap 29 to set the medicament delivery 1 in a ready to mix state. When the front cap 29 has been removed, the delivery member cover 5 is moved in the proximal direction to a ready to mix position due to it being biased in the proximal direction by the second resilient member 18. This situation is shown in FIG. 9, with the arrow showing that the delivery member cover 5 is moved in the proximal direction. The delivery member cover 5 is axially locked with the coupling sleeve 7, which is axially locked with the triggering member 13. The proximal movement of the delivery member cover 5 hence causes corresponding proximal movement of the triggering member 13. The rotator sleeve 11 is however axially locked relative to the housing structure 3 by means of its engagement with the thread structure 3c of the housing structure 3. The triggering member 13 is thus moved proximally relative to the rotator sleeve 11. The rotator sleeve threads 11c and the triggering member threads 13e hence become axially aligned, as shown in FIG. 10. The triggering member 13 thereby obtains its ready to mix position.

The medicament container is a mixing type of medicament container. The medicament container hence has a proximal chamber which the distally pointing needle portion enters when the front cap 29 is unscrewed and the septum is pierced. The proximal chamber may contain a "drug cake", i.e. a freeze-dried medicament. The medicament container may comprise a distal chamber filled with a liquid such as water. The proximal chamber and the distal chamber are separated by a plunger. The medicament container also has one or more bypass channels.

The plunger is prior to mixing arranged distally relative to the bypass channels. During mixing, the medicament container is moved in the distal direction as the delivery member cover 5, the coupling sleeve 7, the medicament container holder 9, the rotator sleeve 11 and the triggering member 13 are all being rotated concurrently and thereby moved in the distal direction. Due to the distal movement of the medicament container, the plunger rod is pushed further into the medicament container. This results in a pressure increase in the distal chamber, causing the plunger to move in the proximal direction until it reaches the bypass channels. When the plunger reaches the bypass channels, the liquid is able to flow past the plunger and into the proximal chamber to mix with the freeze-dried medicament.

Figure 11:
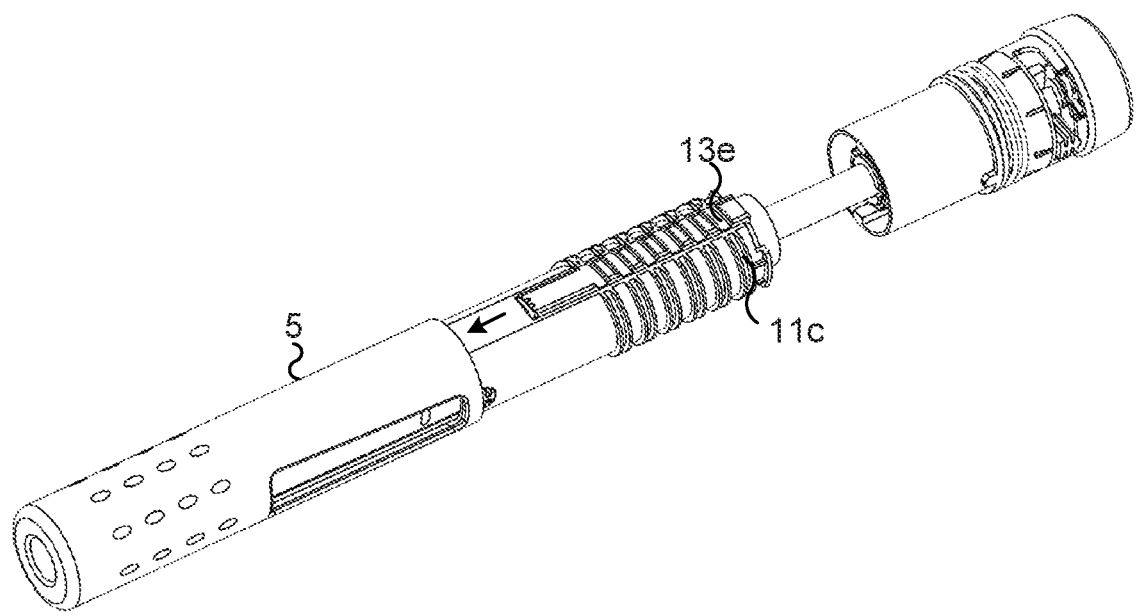
FIG. 11 is a perspective view of the medicament delivery device in FIG. 10 with the housing structure removed to expose the interior of the device.
Figure 12:
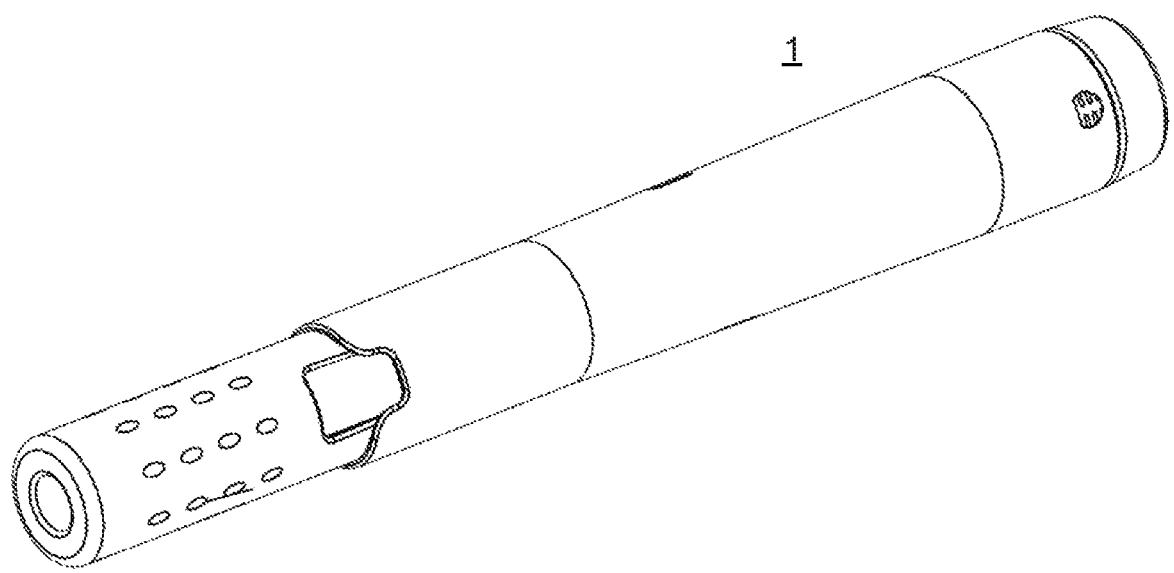
FIG. 12 is a perspective view of the medicament delivery device in FIG. 1 in a dose setting state/position.

FIG. 11 shows the medicament delivery device 1 after the mixing procedure. In order to perform the mixing procedure the medicament delivery device 1 is first set in the ready to mix state, in which the rotator sleeve 11 and the triggering member 13 are in a threaded connection with the thread structure 3c of the housing structure 3 according to the configuration in FIG. 10, by removing the front cap 29. Mixing is hence performed after the front cap 29 has been removed, in order to set the medicament delivery device 1 in a state ready for medicament administration. The mixing is a manual mixing procedure. In order to mix, the user rotates the delivery member cover 5 relative to the housing structure 3. Mixing is in particular performed due to rotation of the delivery member cover 5 relative to the housing structure 3, and while the user rotates the delivery member cover 5 relative to the housing structure 3. The delivery member cover 5 is rotated relative to the housing structure 3 such that the thread segments 3d of the thread structure 3c move from the most distal thread of the rotator sleeve 11 and the triggering member 13 to the most proximal thread, until the engagement members 3e reach their position between the barriers 13h, preventing further rotation of the delivery member cover 5 relative to the housing structure 3. This situation is shown in FIG. 12. At this time, a trailing edge of a thread segment 3d has already moved past the blocking structure 11e, preventing backwards rotation. In this position the triggering member 13 has obtained a dose setting position. Since the engagement members 3e are positioned between respective pairs of barriers 13h, i.e. in the planar portions 13g, the triggering member 13 may now be moved in the distal direction.

Figure 13:
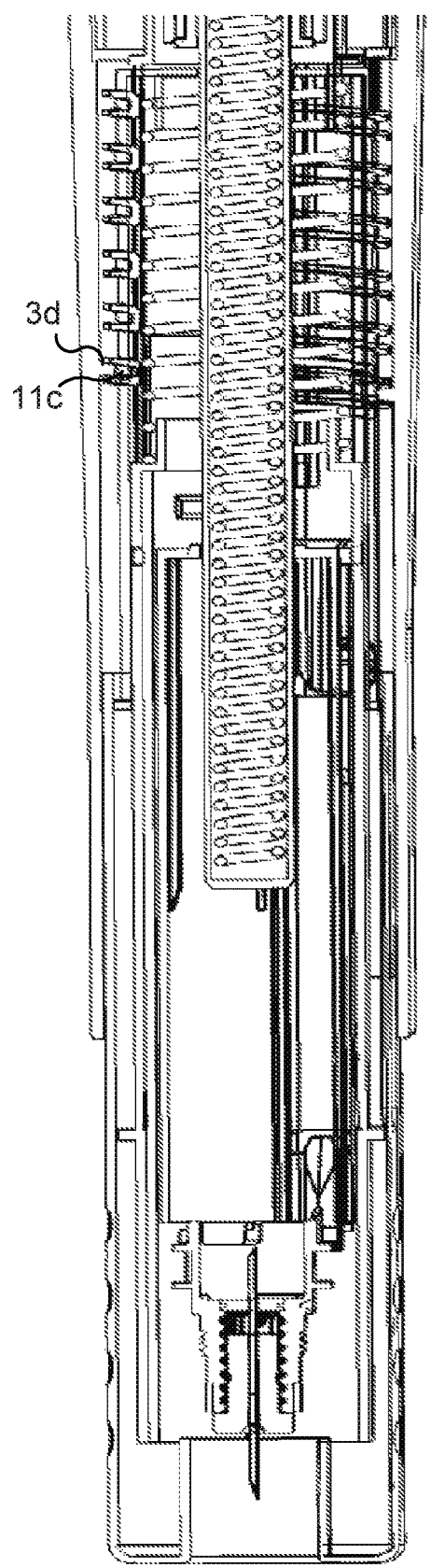
FIG. 13 is a longitudinal section of the medicament delivery device in FIG. 12.

FIG. 13 shows that an engagement member 3e is arranged in a planar portion 13g, enabling the triggering member to move in the distal direction relative to the housing structure 3.

Figure 14:
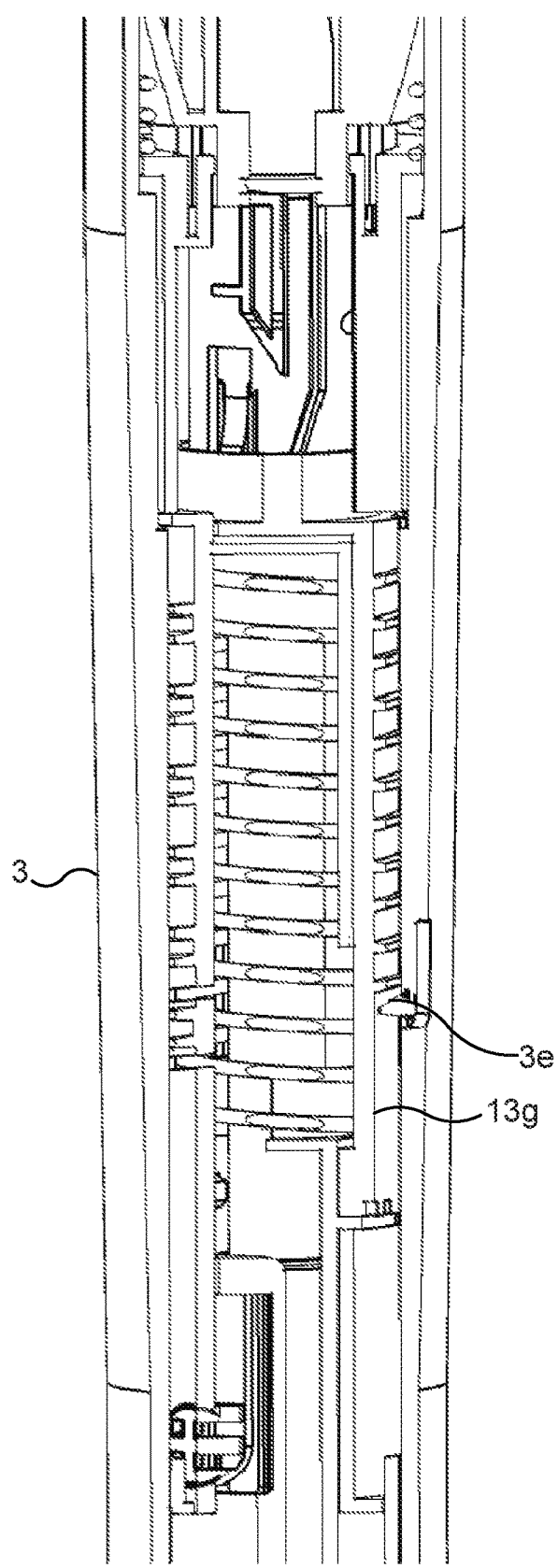
FIG. 14 shows the interior of the medicament delivery device in FIG. 12 from a different view.
Figure 15:
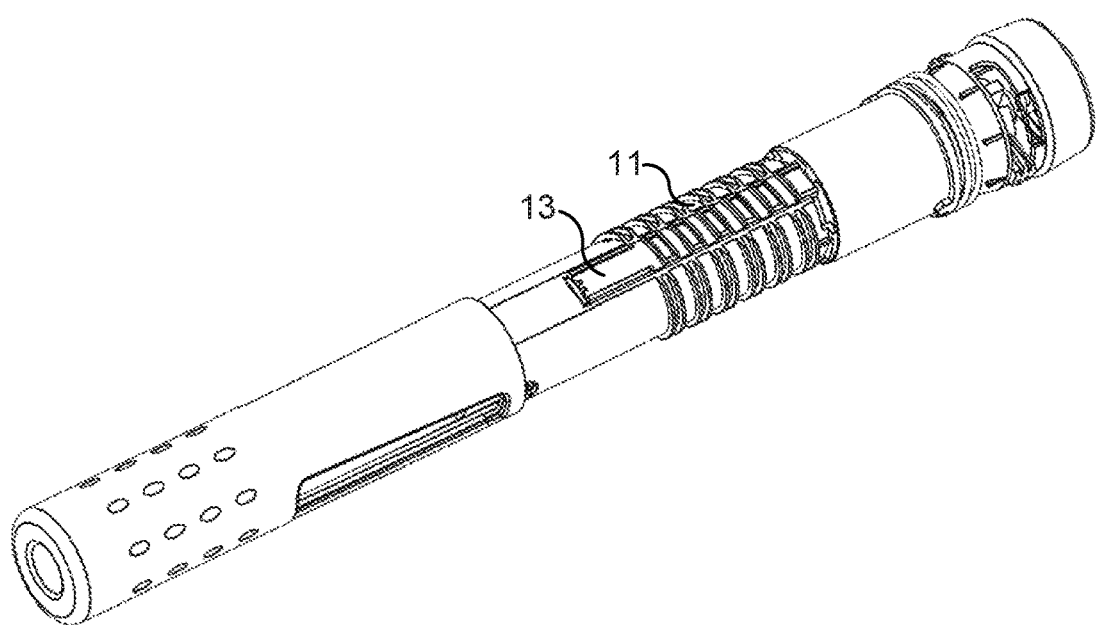
FIG. 15 is a perspective view of the medicament delivery device in FIG. 13 with the housing structure removed to expose the interior of the device.

FIG. 14 depicts the medicament delivery device 1 when the triggering member 13 is in the dose setting position. In this state of the medicament delivery device 1, a user may set the dose before. The dose setting is performing prior to medicament administration. When the rotator sleeve 11 is moved distally during mixing and the triggering member 13 is moved towards the dose setting position, the rotator sleeve 11 pushes the clutch member 21 from a first position, towards the distal end of the medicament delivery device 1 such that the housing structure engagement structure 21a moves out from its engagement with the housing structure 3 via a recess 3f. The clutch member 21 thereby obtains a second position in which it is able to rotate relative to the housing structure 3. Since the clutch member 21 and the dose knob 23 are rotationally locked relative to each other, the dose knob 23 is also released from its rotational locked state together with the clutch member 21.

Figure 16:
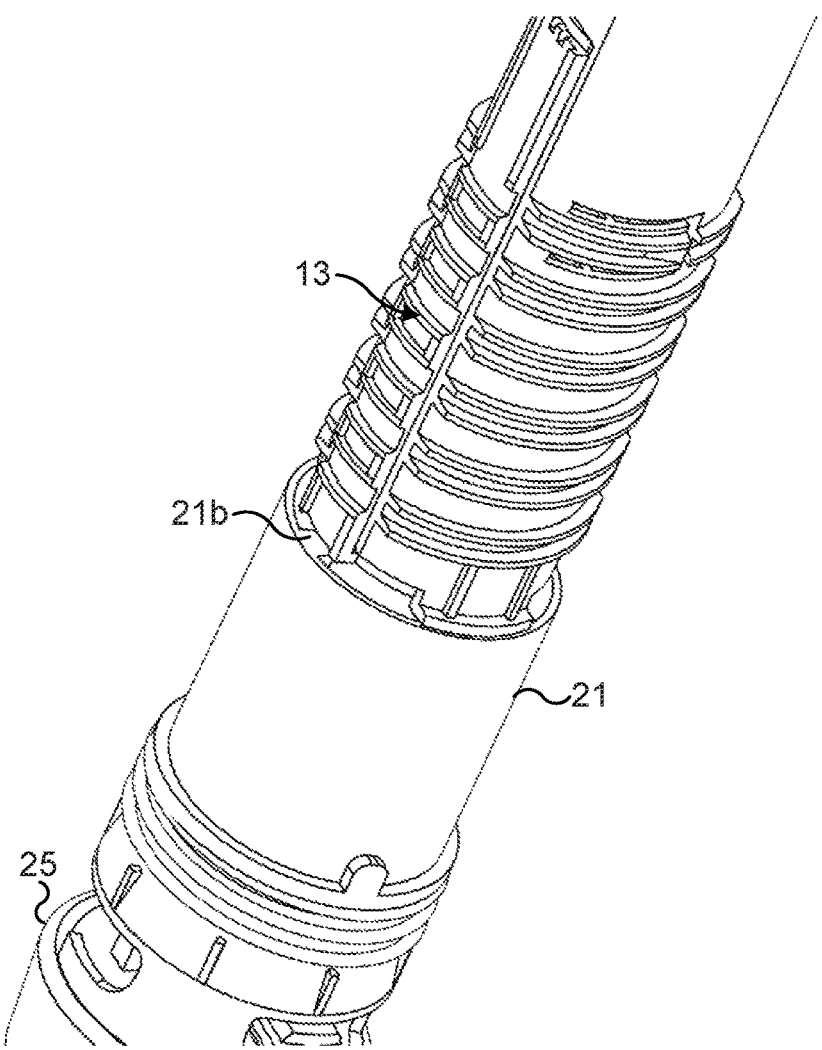
FIG. 16 shows a perspective view of a distal end portion of the medicament delivery device during dose setting.
Figure 17:
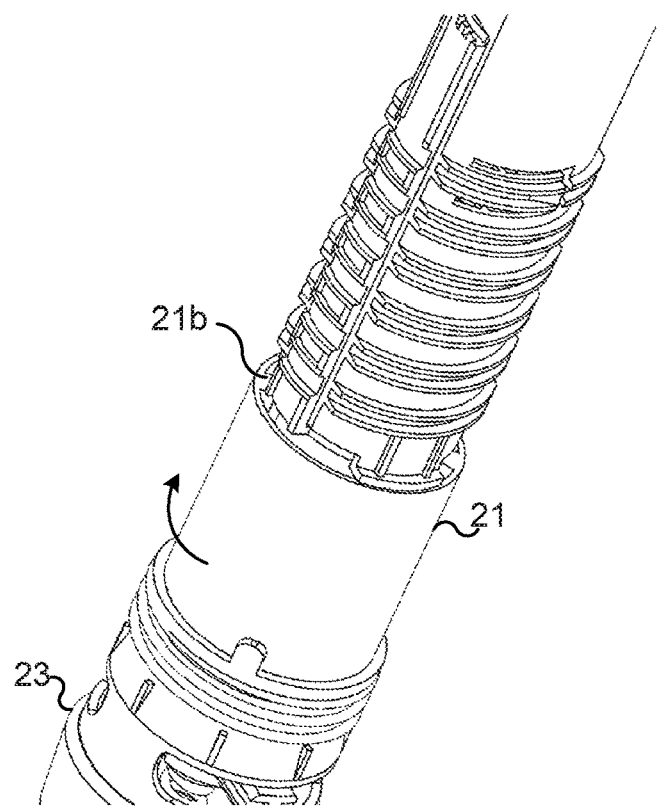
FIG. 17 shows a perspective view of a distal end portion of the medicament delivery device during dose setting.
Figure 18:
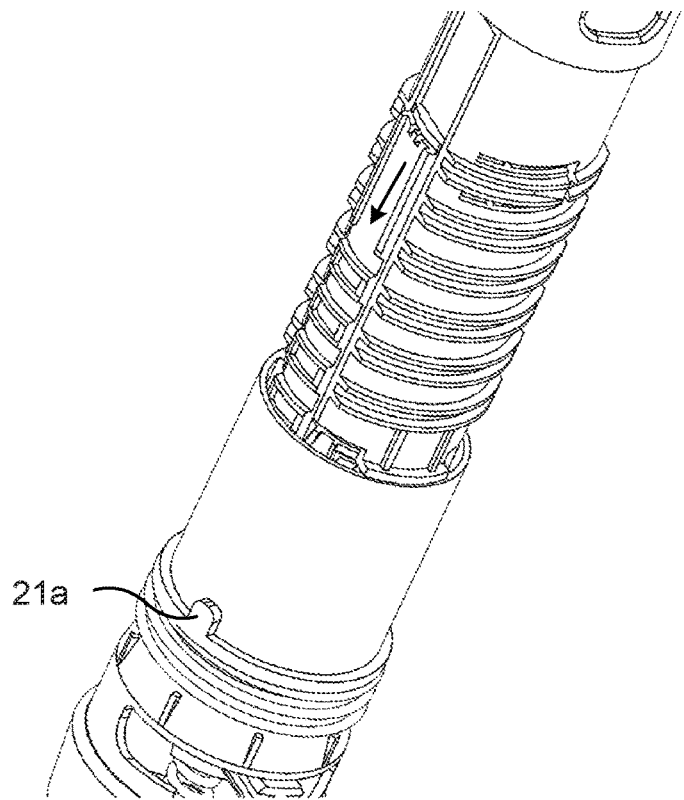
FIG. 18 shows a perspective view of a distal end portion of the medicament delivery device during medicament administration.

FIG. 16 shows the clutch member 21 in the second position. The clutch member 21 has a triggering member blocking structure 21b configured to prevent the triggering member 13 from moving in the distal direction from the dose setting position as long as the clutch member 21 has not been rotated, i.e. as long as no dose has been set by the dose knob 23. The delivery member cover 5 is hence also prevented from moving axially in the distal direction at this point. The triggering member blocking structure 21b is in this example a radially inwards extending structure arranged distally relative to the distal end of the triggering member 13. When the dose knob 23 is rotated to set a dose, the clutch member 21 is also rotated, and the triggering member blocking structure 21b is rotated as well, as shown in FIG. 17, where the clutch member 21 and the dose knob 23 have been rotated as shown by the arrow. This rotation is performed by a user, and in case the medicament delivery device 1 is designed to be able to provide one of several user-selected doses, the selected dose is determined by the amount of rotation of the dose knob 23. The triggering member blocking structure 21b is hence moved in the circumferential direction out of the way of the triggering member 13, enabling the triggering member 13 to be moved in the distal direction, as shown in FIG. 18 (however for a different amount of rotation and hence a different dose, as can be seen by the different circumferential position of the housing structure engagement structure 21a).

Figure 19:
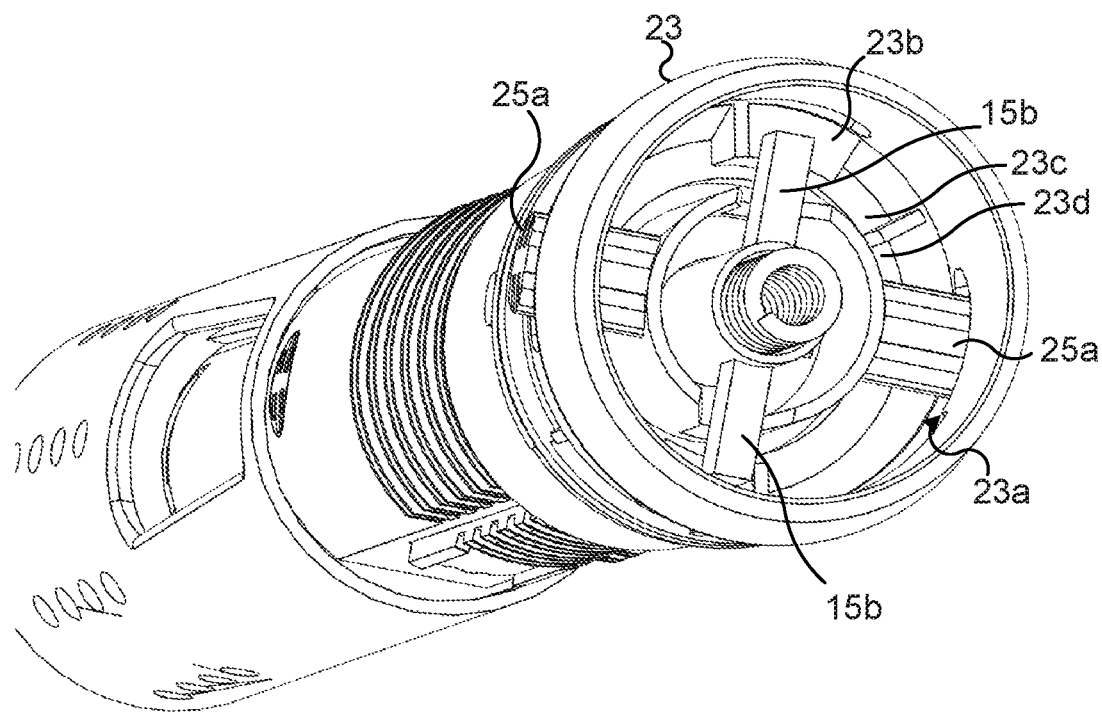
FIG. 19 shows a perspective view of a distal end of the medicament delivery device in a dose setting procedure.
Figure 20:
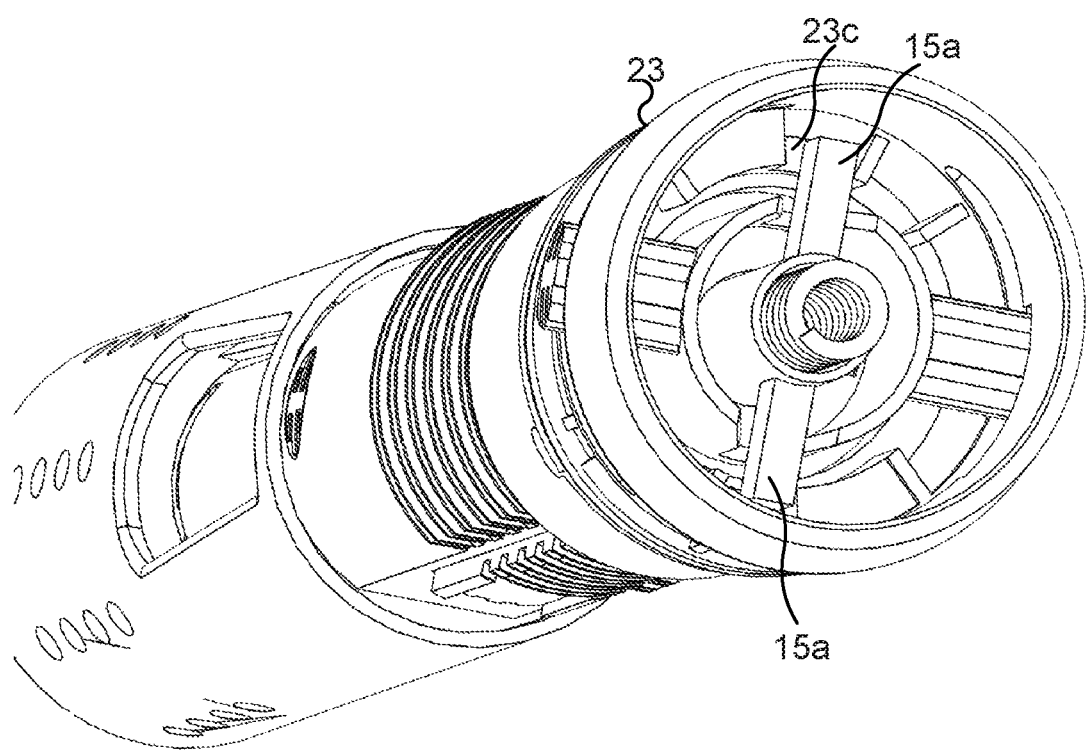
FIG. 20 shows a perspective view of a distal end of the medicament delivery device in a dose setting procedure.
Figure 21:
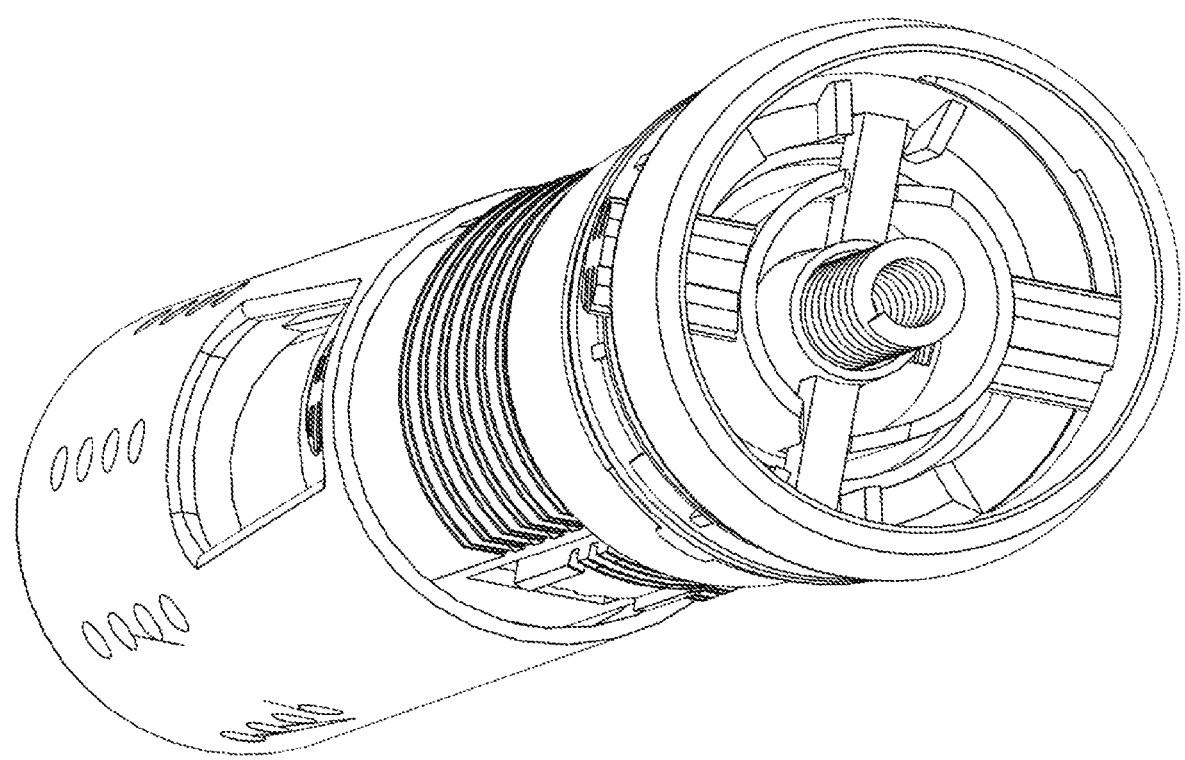
FIG. 21 shows a perspective view of a distal end of the medicament delivery device after medicament administration.

The dose setting as such is described with reference to FIGS. 19-21. In FIG. 19 no dose has been set. The dose setting protrusions 15b of the plunger rod 15 rest on an elevated structure 23b of the dose knob 23. The dose knob 23 comprises plunger rod stop surfaces 23c-23d each of which is distanced further away from the distal end 3b of the housing structure 3 than the elevated structures 23b. The plunger rod stop surfaces 23c-23d may have a staircase configuration with a separating wall between each adjacent step. By rotating the dose knob 23, the plunger rod guide member 25, which has guide structures 25a received by the recesses 23a of the dose knob 23 is rotated such that the dose setting protrusions 15b of the plunger rod 15 become axially aligned with the desired plunger rod stop surfaces 23c-23d, as shown in FIG. 20. The elevation or distance of the plunger rod stop surfaces 23c from the dose setting protrusions 15b defines the stroke length of the plunger rod 15 during medicament administration.

When the dose has been set, the delivery member cover 5 can be pushed into the housing structure 3. The triggering member 13 will then be able to move towards the distal end 3b of the housing structure 3. A user may hence set the delivery member cover 5 in contact with the injection site and press the medicament delivery device 1 towards the injection site, causing the delivery member cover 5 to move axially into the housing structure 3 towards the distal end 3b of the housing structure 3. By moving the delivery member cover 5 and hence the triggering member 13 in the distal direction, the rotator engagement structures 13b cooperate with the guide tracks 19a of the rotator 19, causing the rotator 19 to rotate and thus to release the plunger rod 15. The plunger rod 15 is thereby able to move in the proximal direction the axial distance between the dose setting protrusions 15b and the plunger rod stop surfaces 23c selected when setting the dose, as shown in FIG. 21.

The invention claimed is:

1. A mix and triggering assembly for a medicament delivery device, comprising:
   a housing structure having a proximal end and a distal end,
   a delivery member cover,
   a rotator sleeve, and
   a triggering member configured to move axially relative to the rotator sleeve,
   wherein the delivery member cover, the rotator sleeve and the triggering member are received by the housing structure, where the delivery member cover is configured to extend from the proximal end of the housing structure and the triggering member is rotatably locked with the rotator sleeve and the delivery member cover,
   wherein the delivery member cover, the rotator sleeve and the triggering member are rotatably arranged relative to the housing structure,
   wherein the housing structure has a thread structure and the triggering member has external triggering member threads configured to cooperate with the thread structure, where the rotator sleeve and the triggering member are in a threaded connection with the thread structure when the triggering member is in a ready to mix position that prevents irrotational axial movement of the triggering member relative to the housing structure towards the distal end of the housing structure,
   wherein rotation of the delivery member cover relative to the housing structure causes the rotator sleeve and the triggering member to be screwed from the ready to mix position towards the distal end of the housing structure until the triggering member reaches a dose setting position such that the triggering member is released from engagement with the thread structure and enabling irrotational axial movement of the triggering member further towards the distal end of the housing structure.

2. The mix and triggering assembly of claim 1, wherein the thread structure has an engagement member configured to snap-fit with the external triggering member threads of the triggering member to prevent irrotational axial movement of the triggering member from the ready to mix position to the dose setting position.

3. The mix and triggering assembly of claim 1, wherein the triggering member is biased towards the proximal end of the housing structure, and in an initial default position the delivery member cover is axially locked relative to the housing structure in a partly received position in the housing structure, wherein the triggering member is movable axially towards the proximal end of the housing structure when the delivery member cover is released from the initial default position to set the triggering member from the initial default position to the ready to mix position, in which the delivery member cover extends proximally further from the housing structure relative to the partly received position.

4. The mix and triggering assembly of claim 3, wherein the thread structure has an engagement member configured to snap-fit with the external triggering member threads of the triggering member to prevent irrotational axial movement of the triggering member from the ready to mix position to the dose setting position and wherein the engagement member allows irrotational axial movement of the triggering member from the initial default position towards the proximal end of the housing structure to move to the ready to mix position.

5. The mix and triggering assembly of claim 1, wherein the rotator sleeve has a blocking structure configured to engage with a thread segment of the thread structure of the housing structure when the triggering member is in the dose setting position to prevent rotation of the rotator sleeve back towards the proximal end of the housing structure.

6. The mix and triggering assembly of claim 5, wherein the thread structure includes a plurality of disjoint thread segments in a circumferential direction, wherein the blocking structure is configured to bear against a radial edge of the thread segment to prevent rotation of the rotator sleeve back towards the proximal end of the housing structure.

7. The mix and triggering assembly of claim 1, wherein the triggering member has two legs and the rotator sleeve has chamfered faces, wherein the legs are configured to extend along a respective chamfered face towards the proximal end of the housing structure.

8. The mix and triggering assembly of claim 7, wherein the triggering member has axially extending barriers configured to delimit circumferential movement of an engagement member when the triggering member is in the dose setting position, thereby preventing further rotation of the triggering member towards the distal end of the housing structure.

9. The mix and triggering assembly of claim 8, wherein the axially extending barriers pairwise form part of a proximal end portion of a respective leg of the triggering member.

10. The mix and triggering assembly of claim 9, wherein each leg has a planar portion arranged between the pairs of barriers to enable linear movement of the engagement member between the pairs of barriers of a leg.

11. The mix and triggering assembly of claim 1, comprising a clutch member and a dose knob configured to be rotationally locked with the clutch member, wherein the rotator sleeve is configured to push the clutch member towards the distal end of the housing structure when the triggering member is moved towards the dose setting position, causing the clutch member to move distally inside the housing structure from a first position in which it is rotationally locked with the housing structure to a second position in which it is able to rotate relative to the housing structure, enabling rotation of the dose knob relative to the housing structure.

12. The mix and triggering assembly of claim 11, wherein the clutch member has a triggering member blocking structure configured to block the triggering member from movement from the dose setting position towards the distal end of the housing structure when the clutch member is in the first position.

13. The mix and triggering assembly of claim 12, wherein the dose knob is able to rotate the clutch member such that the triggering member blocking structure is rotated and releases the triggering member, enabling the triggering member to move towards the distal end of the housing structure.

14. The mix and triggering assembly of claim 13, comprising a rotator and a plunger rod, wherein the triggering member is able to cause rotation of the rotator when the delivery member cover moves the triggering member from the dose setting position towards the distal end of the housing structure, releasing the plunger rod.

15. A medicament delivery device comprising the mix and triggering assembly of claim 1.

16. The medicament delivery device of claim 15 further comprising a dual chambered medicament container.

17. The medicament delivery device of claim 16 further comprising a cap that, when rotated relative to the housing structure, causes a distal end of a double ended needle to pierce a septum in the dual chambered medicament container.

18. A mix and triggering assembly for a medicament delivery device, comprising:
  a housing structure having an inside surface comprising a thread structure and having a proximal end and a distal end,
  a delivery member cover threadedly engaged with the thread structure and configured to extend from the proximal end of the housing structure,
  a rotator sleeve, and
  a triggering member rotatably locked with the rotator sleeve and the delivery member cover and configured to move axially relative to the rotator sleeve, where the triggering member has external triggering member threads that cooperate with the thread structure, where the rotator sleeve and the triggering member are in a threaded connection with the thread structure when the triggering member is in a ready to mix position that prevents irrotational axial movement of the triggering member relative to the housing structure towards the distal end of the housing structure,
  wherein rotation of the delivery member cover relative to the housing structure causes the rotator sleeve and the triggering member to be moved from the ready to mix position towards the distal end of the housing structure until the triggering member reaches a dose setting position whereby the triggering member is disengaged from the thread structure to enable irrotational axial movement of the triggering member further towards the distal end of the housing structure,
  wherein the triggering member is biased towards the proximal end of the housing structure and the delivery member is in an initial default position such that the delivery member cover is axially locked relative to the housing structure in a partly received position within the housing structure,
  wherein the triggering member is movable axially towards the proximal end of the housing structure when the delivery member cover is released from the initial default position to set the triggering member to the ready to mix position where the delivery member cover extends proximally a greater distance from the housing structure relative to the partly received position.

19. The mix and triggering assembly of claim 18, wherein the rotator sleeve has a blocking structure configured to engage with disjoint thread segments of the thread structure of the housing structure when the triggering member is in the dose setting position so as to prevent rotation of the rotator sleeve back towards the proximal end of the housing structure.

20. The mix and triggering assembly of claim 18, wherein the rotation of the delivery member cover causes a dual chambered medicament container to move distally and engage a stationary plunger rod positioned within the housing structure.

* * * * *